United States Patent [19]
Kawaguchi

[11] Patent Number: 4,849,032
[45] Date of Patent: Jul. 18, 1989

[54] ORTHODONTIC COIL SPRING AND METHOD OF MAKING THE SAME

[75] Inventor: Kozo Kawaguchi, Futaba, Japan

[73] Assignee: Tomy, Inc., Fukushima, Japan

[21] Appl. No.: 169,384

[22] Filed: Mar. 17, 1988

[30] Foreign Application Priority Data

Mar. 18, 1987 [JP] Japan ............................. 62-38536[U]
Mar. 24, 1987 [JP] Japan ............................. 62-43091[U]

[51] Int. Cl.$^4$ .............................................. C22F 1/10
[52] U.S. Cl. ........................ 148/11.5 R; 148/11.5 N; 148/402; 420/902
[58] Field of Search ................ 148/11.5 R, 11.5 N, 148/402; 420/902

[56] References Cited
PUBLICATIONS

20 Kirk–Othmer, *Encyclopedia of Chemical Technology*, 726 733 (3d ed. 1982) New York.

*Primary Examiner*—R. Dean
*Attorney, Agent, or Firm*—Kenyon & Kenyon

[57] ABSTRACT

An orthodontic coil spring is made of a shape-memory alloy wire which is wound into a coil and heat treated into a superelastic state. The coil spring imparts a predetermined spring force within a superelastic zone of deflection.

11 Claims, 5 Drawing Sheets

ORTHODONTIC COIL SPRING AND METHOD OF MAKING THE SAME

BACKGROUND OF THE INVENTION

1. Field of the Invention

The invention relates to orthodontic devices, and more particularly, to orthodontic coil springs for mounting to a patient's teeth in order to impart a force to move the teeth.

2. Background Information

In FIGS. 1A and 1B a conventional system for orthodontic treatment is illustrated, wherein each tooth 1 has attached to a surface thereof an orthodontic bracket 2. An archwire 3 is connected to each bracket 2 in order to impart a force to straighten the teeth.

In cases where there is a space between adjacent teeth, such as, for example, the space 4 between teeth 1a and 1b, stop fittings 5 are attached to each bracket 2 of the adjacent teeth. A coil spring is then utilized to connect the two stop fittings and impart a force to move the adjacent teeth into the space 4. In FIG. 1A, a tension spring 6 is shown, having formed on each end hooks 6a which are each connected to a stop fitting 5. The force of the tension spring 6 imparts a force in order to move the teeth 1a and 1b toward one another and into the space 4, as indicated by the arrows in FIG. 1A.

In an alternative system shown in FIG. 1B, a compression spring 7 is fitted over the archwire 3 and between the orthodontic brackets 2 of adjacent teeth 1c and 1d. The force of the compression spring 7 acts to move the tooth 1c away from the tooth 1d and into the space 4, as indicated by the arrow in FIG. 1B.

The known orthodontic coil springs, such as the tension spring 6 or compression spring 7, have been formed of stainless steel. The mechanical properties of stainless steel springs are such that the magnitude of the spring force changes sharply with slight deflections in the spring. In FIG. 2, the deflection-spring force curve for a typical stainless steel tension coil spring is shown X2, and in similar manner, in FIG. 3, the deflection-spring force curve for a typical stainless steel compression coil spring is shown Y2. As can be seen, in both cases, the spring force changes sharply with increasing or decreasing deflection of the spring. Accordingly, one problem associated with conventional stainless steel springs is that after the teeth are caused to move, even slightly, the deflection causes the spring force to decrease and become insufficient to move the teeth as desired.

One method that has been used to compensate for the problem of decreasing spring force in stainless steel springs has been to increase the initial deflection of the spring. As a result, after initial tooth movement the spring can still impart a sufficient force to continue moving the teeth. However, this method has proven to be unsatisfactory since the initial force of the spring is generally too great and as a result, causes pain and discomfort to the patient. Moreover, this method fails to overcome the inherent problem of the relatively sharp changing spring force with deflections in the spring.

One consequence of this problem is that orthodontists have been relegated to frequently changing the stainless steel coil springs so that after there is even slight tooth movement new springs are inserted in order to maintain the optimal spring force against the teeth. This method has proven particularly troublesome in replacing compression coil springs such as spring 7, shown in FIG. 1B. As can be seen, in order to replace the compression spring 7 the archwire 3 must first be disconnected from the orthodontic bracket 2 and then reconnected in order to first remove and then insert a new spring 7.

It is known in the art that the orthodontic forces imparted on one-root front teeth and two-root small molars should be about one quarter to one half of that imparted on three-root large molars. It is required therefore, to correspond the spring force to the type of tooth to be moved. If the spring force is too great for example, the teeth can be improperly rotated or shifted.

The spring force of conventional stainless steel coil springs can only be roughly determined by varying the wire diameter and winding diameter of the spring. Accordingly, one problem associated with conventional stainless steel coil springs is that the optimal spring force necessary for a particular orthodontic application cannot be accurately set for each spring. Moreover, it has not been possible to produce conventional springs that are identical in size yet have different loading characteristics. As a result, it has proven particularly difficult to obtain the optimum spring force to move a particular tooth with conventional stainless steel springs.

Another problem associated particularly with conventional compression coil springs, such as the spring 7 in FIG. 1B, is that because the spring is inserted over the archwire 3, the minimal dimension of the winding diameter of the spring is limited by the diameter of the archwire. The loading characteristics of the spring therefore are also limited as a result of the minimum dimension.

In order to obtain the most suitable spring force with conventional coil springs, the spring is generally trimmed to a length believed to be suitable as determined by measuring the distance of the space between the particular teeth to be moved. Known spring testers or push-pull gauges, not shown, are then utilized in order to set the spring force for the particular size of the space. This process must be repeated with each successive change in springs in order to maintain the optimum spring force for the particular tooth to be moved. Accordingly, the use of conventional orthodontic springs has been particularly time consuming and troublesome.

It is an object of the invention therefore to provide an orthodontic coil spring that overcomes the problems and disadvantages of known coil springs.

It is a further object of the invention to provide an orthodontic coil spring having a preset spring force which is determined for use with a particular tooth to be moved.

It is yet a further object of the invention to provide an orthodontic coil spring for imparting a predetermined and substantially constant spring force throughout a zone of deflection of the spring sufficient to cover the desired movement of a tooth.

Other objects and advantages of the orthodontic coil spring of the invention will become apparent in view of the following detailed description and drawings taken in connection therewith.

SUMMARY OF THE INVENTION

The invention is directed to an orthodontic coil spring comprising a shape-memory alloy wire which is wound into a coil and heat treated into a superelastic state so that it imparts a predetermined spring force within a superelastic zone of deflection of the coil spring.

Another coil spring of the invention comprises a shape-memory alloy wire which is heat treated into a superelastic state and wound into a close contact shape. The coil spring of the invention imparts a predetermined spring force upon even slight deflection of the spring.

In accordance with a method of the invention, an orthodontic coil spring is made by winding a shape memory alloy wire into a coil spring. The coil is then heated for a fixed period of time within a fixed temperature range into a superelastic state for developing a predetermined spring force within a superelastic zone of deflection of the coil spring.

In accordance with another method of the invention, a tension coil spring is made by winding a shape-memory alloy wire into a coil having spaced pitch intervals. The coil is then heated for a fixed period of time within a fixed temperature range into a superelastic state for developing a predetermined spring force within a superelastic zone of deflection of the coil. The coil is then wound in the opposite direction of the first winding into a coil spring having a close contact shape so that the coil is formed with initial tension for imparting a predetermined spring force upon even slight coil deflection.

DESCRIPTION OF PREFERRED EMBODIMENTS

Figure 4:
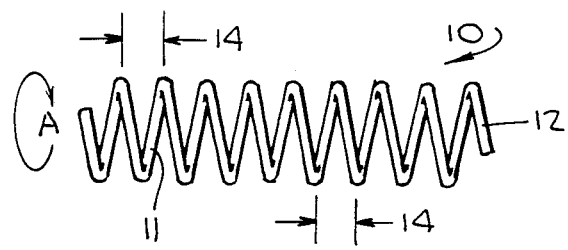
FIG. 4 is a planar view illustrating a compression coil spring embodying the invention.

In FIG. 4, a compression coil spring embodying the invention is illustrated 10. The compression spring 10 is formed of a shape-memory alloy wire 12, which is preferably made of a nickel-titanium alloy. The spring 10 is formed by cutting the wire 12 to an appropriate length and then winding the wire onto the core of a known coiling machine, not shown, so that the spring 10 is formed with fixed pitch intervals, shown typically 14. Alternatively, the wire 12 may be first wound onto the core of a coiling machine, and then cut into one or more segments to form each spring 10. The compression spring 10 is then heat treated to a superelastic state for a fixed period of time within a fixed temperature range in order to set the desired spring force, as will be described in further detail below.

Figure 5:
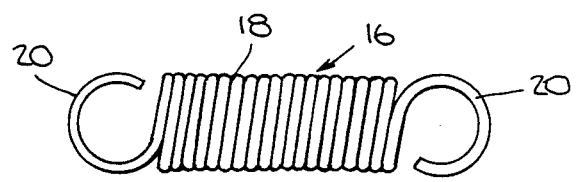
FIG. 5 is a planar view illustrating a tension coil spring embodying the invention.

Turning to FIG. 5, a tension coil spring embodying the invention is illustrated 16. The tension spring 16 is formed of a shape-memory alloy wire 18, which is preferably made of a nickel-titanium alloy, and is the same as the wire 12 described above in relation to FIG. 2 of the previous embodiment. The tension spring 16 is formed by cutting the wire 18 to an appropriate length and then winding the wire onto the core of a known coiling machine, not shown, and into a close contact shape, as shown in FIG. 5. Alternatively, the wire 18 may be first wound onto the core of coiling machine, and then cut into one or more segments to form each spring 16. Each end of the wire 18 is then formed into an end hook 20 for purposes of connecting the tension spring 16 to other orthodontic appliances, not shown. As described above in relation to the previous embodiment, the tension spring 16 is also heat treated to a superelastic state for a fixed period of time within a fixed temperature range in order to set the desired spring force.

Figure 2:
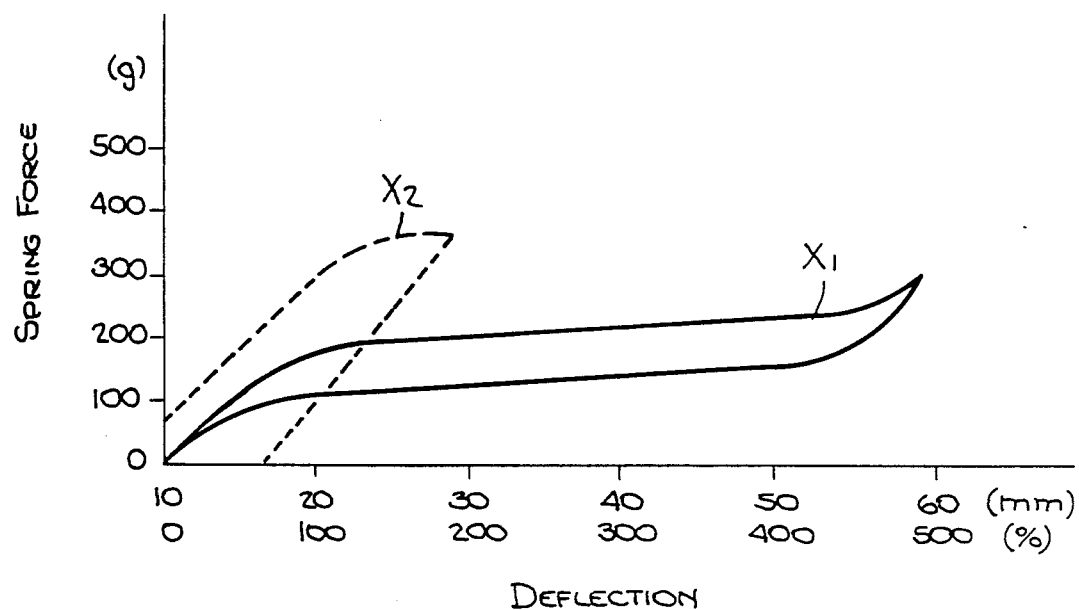
FIG. 2 is a graph comparing the deflection-spring force curves of a tension coil spring embodying the invention and a conventional tension coil spring.
Figure 3:
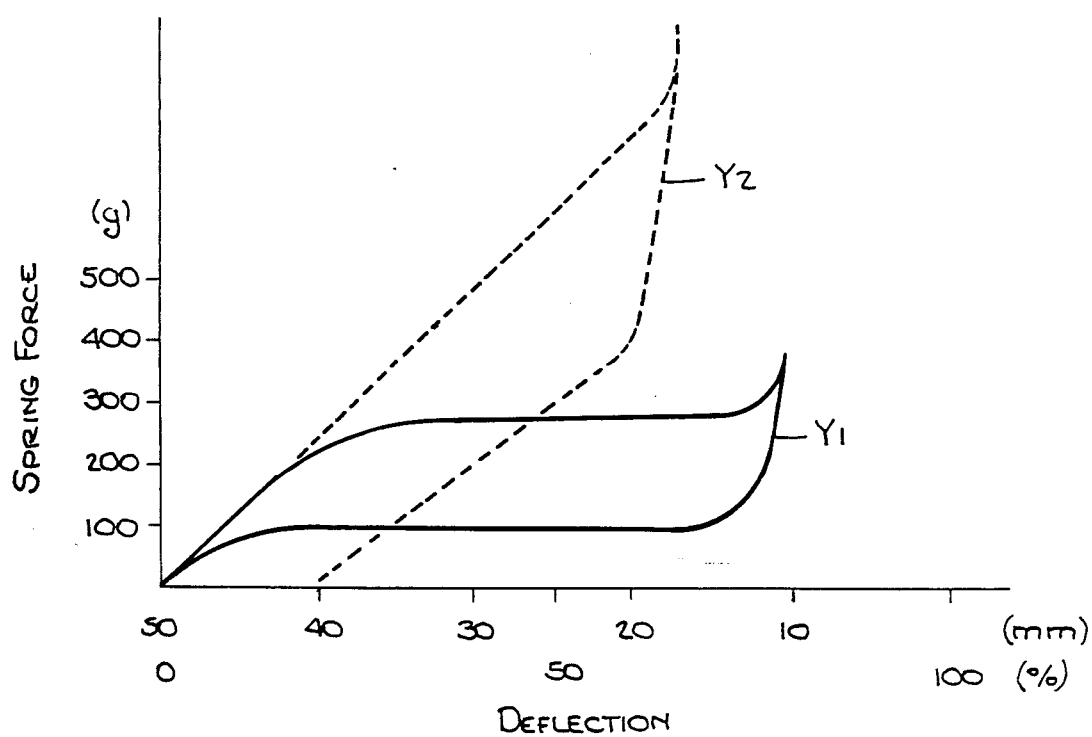
FIG. 3 is a graph comparing the deflection-spring force curves of a compression coil spring embodying the invention and a conventional compression coil spring.

As shown in FIG. 2, the deflection-spring force curve for a tension coil spring embodying the invention is shown X1, as compared to that for a conventional tension coil spring X2. Similarly, in FIG. 3, the deflection-spring force curve for a compression coil spring Y1 is compared to that for a conventional coil spring Y2. As can be seen in both FIGS. 2 and 3, the springs of the invention impart a substantially constant spring force throughout a relatively wide range of deflection, known as the superelastic zone of deflection, whereas the spring force of each of the conventional springs increases sharply with increasing deflection. As a result, the coil springs of the invention can be employed to impart a predetermined and substantially constant spring force throughout the entire movement of a tooth, unlike conventional springs which have to be frequently changed or adjusted with incremental tooth movement.

Figure 6:
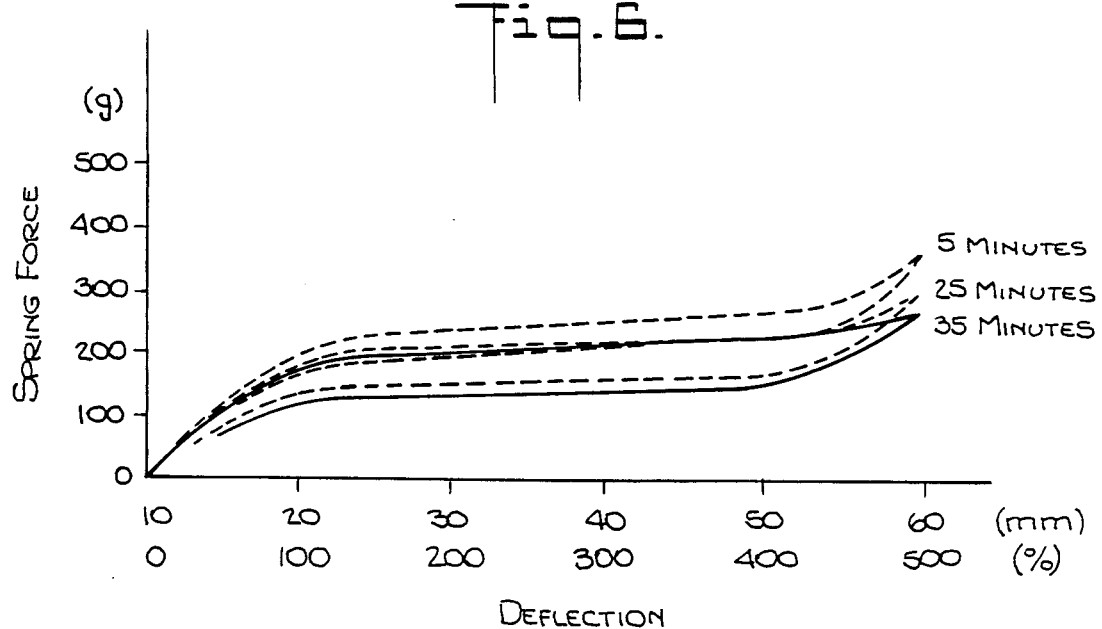
FIG. 6 is a graph illustrating the relation between the heating time and spring force of a tension coil spring embodying the inventon.
Figure 7:
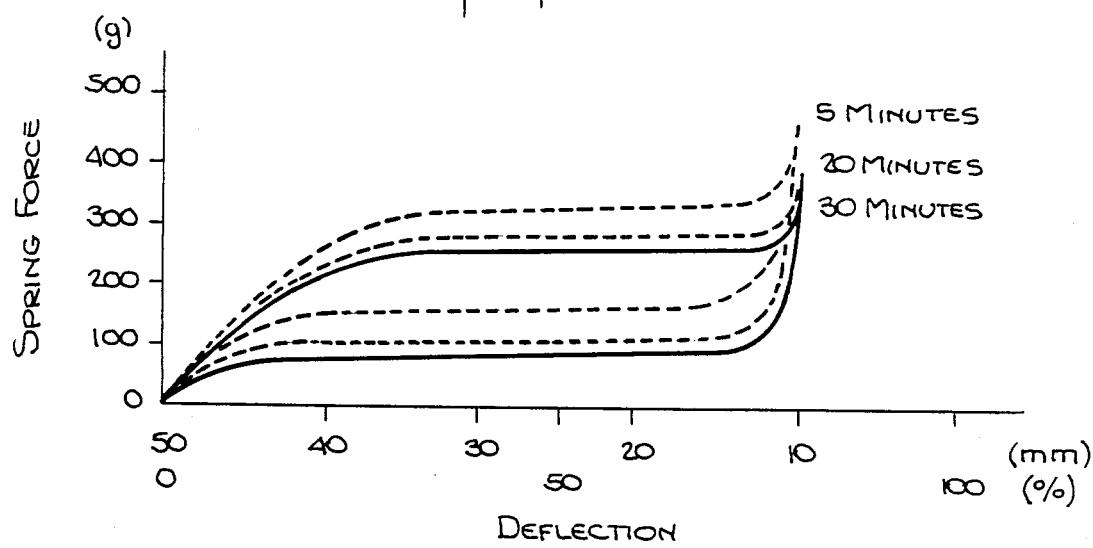
FIG. 7 is a graph illustrating the relation between the heating time and spring force of a compression coil spring embodying the invention.

Turning to FIGS. 6 and 7, deflection-spring force curves are shown for different heating time periods for exemplary embodiments of tension coil spring 16 and compression coil spring 10, respectively. Each embodiment of the coil spring is formed of a nickel-titanium alloy wire having a 0.090 inch diameter, and which is wound into a 0.030 inch coil diameter. The coil springs are then heat treated at about 500° C. into a superelastic state. It has been determined that by varying the heating time the spring force for wires having the same dimensions can be changed. In FIG. 6, deflection-spring force curves for the tension coil spring 16 are shown for heating time periods of 5 minutes, 25 minutes and 35 minutes. As can be seen, the spring force decreases with increased heating time. In similar manner, in FIG. 7 the deflection-spring force curves for compression coil spring 10 are shown for heating periods of 5 minutes, 20 minutes and 30 minutes. Again, as can be seen, the spring force decreases with increased heating time.

Although FIGS. 6 and 7 show the experimental results for coil springs made of a 0.090 inch diameter wire and wound into a 0.030 inch coil diameter, similar changes in spring force depending upon the heating time will occur in springs of different size. It is found that for a specific sized coil spring, the spring force decreases with increased heating time, as reflected in FIGS. 6 and 7 for the specific exemplary embodiments.

The coil springs embodying the invention are similar to conventional coil springs in that for a fixed coil spring diameter, the spring force decreases with increasing coil diameter. Likewise, for a fixed coil spring length, the spring force increases with increasing wire diameter. However, unlike conventional coil springs, the spring force of the coil springs of the invention can also be determined depending upon the tooth to be moved, or the particular orthodontic application, by varying the heat treatment time for obtaining superelasticity. Moreover, as described above in relation to FIGS. 2 and 3, and as can be seen in FIGS. 6 and 7, the coil springs embodying the invention each impart a substantially constant spring throughout a superelastic zone of deflection. Accordingly, a coil spring embodying the invention can be employed to impart a predetermined and substantially constant spring force throughout the entire movement of a tooth, as described above in relation to FIGS. 2 and 3.

It has been determined from the use of compression coil springs embodying the invention, that the spring force remains substantially the same with changes in the number of windings per unit ooil length. Accordingly, in contrast to conventional coil springs, the winding configuration of the 3 compression springs of the invention can be changed without substantially affecting the spring force of the coil spring.

In ordinary use of the coil springs of the invention, the spring will provide satisfactory results if the desired amount of tooth movement is within the superelastic zone of deflection of the particular spring. However, under certain circumstances, if the spring deflection of a tension coil spring is slight, it may be below the superelastic zone of the spring and accordingly, the spring will impart an insufficient force. This problem is overcome by manufacturing the tension coil spring 16 so that it has initial tension, as hereinafter described in relation to FIGS. 8A to 8C.

Figure 8A:
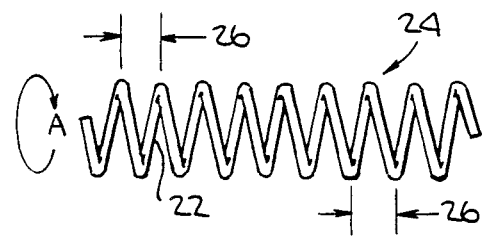
FIGS. 8A to 8C are planar views illustrating a method of making an orthodontic coil spring having initial deflection tension and embodying the invention.

As shown in FIG. 8A, a shape-memory alloy wire 22, which is the same as that described above in relation to the previous embodiments, is wound in the direction indicated by the arrow A onto the core of a known coiling machine, not shown, so that a coil spring 24 is formed having fixed pitch intervals, shown typically 26. The coil spring 24 is then heat treated to a superelastic state, as described above in relation to the previous embodiments.

Figure 8B:
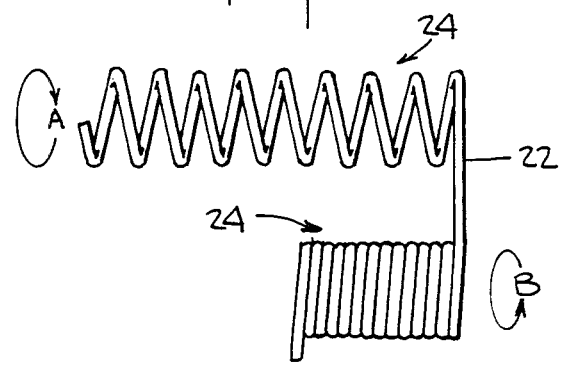
Figure 8C:
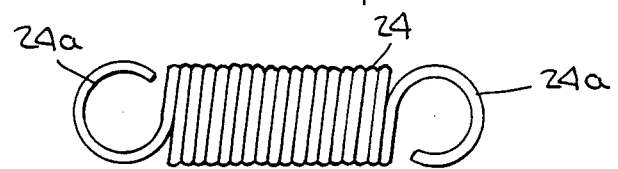

Turning to FIG. 8B, the coil spring 24 is then wound in the direction indicated by the arrow B, which is the opposite direction of the first winding, into a close contact state. It is preferable to trim the coil 24 to the appropriate length prior to the second winding. As shown in FIG. 8C, end hooks 24a are then formed on either end of coil spring 24 for connection to an orthodontic appliance, not shown, for moving a tooth.

The second winding of the coil spring 24 into a close contact shape positively imparts a torsional force to the shape-memory alloy wire 22, so that the coil is formed with an initial tension acting to pull the coil spring 24 into the close contact shape, even when there is no load imparted upon either end of the spring.

Figure 9:
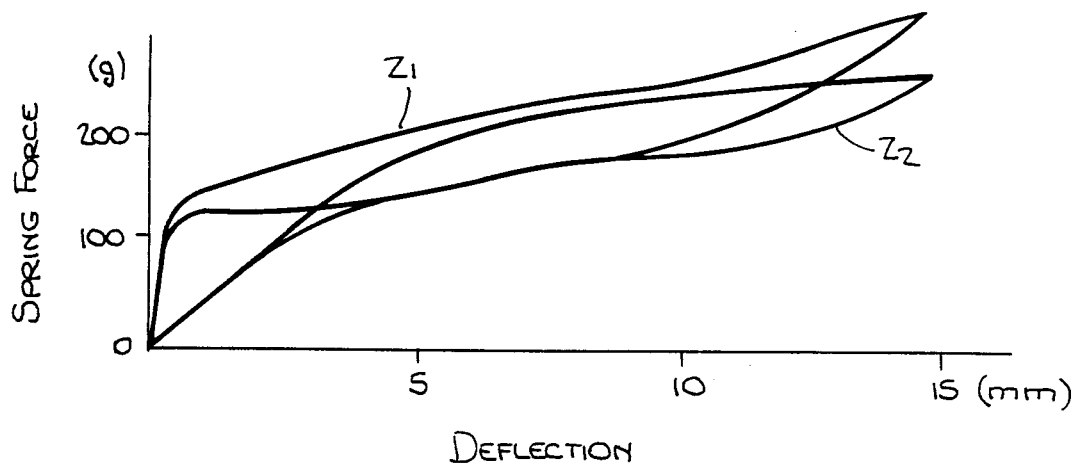
FIG. 9 is a graph comparing the deflection-spring force curves for two orthodontic tension coil springs embodying the invention wherein one spring is made with initial deflection tension.

In FIG. 9, a deflection-spring force curve for a tension coil spring made with initial tension, as described in relation to FIGS. 8A to 8C, is illustrated Z1, and is compared to that of a tension coil spring made in accordance with the previous embodiment described in relation to FIG. 5, and illustrated Z2. As can be seen, the superelastic zone of deflection of the curve Z1 starts at almost zero deflection. Accordingly, an initial tension spring of the invention can impart sufficient force to move a tooth with only slight deflection.

Figure 1A:
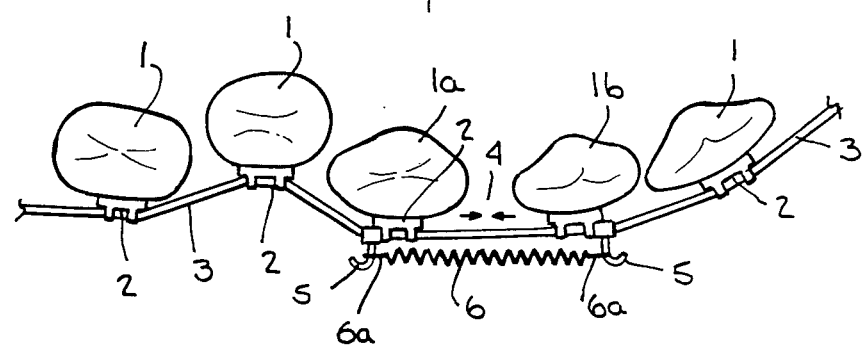
FIG. 1A is a top planar view of a conventional system for orthodontic treatment illustrating the use of a tension coil spring.
Figure 1B:
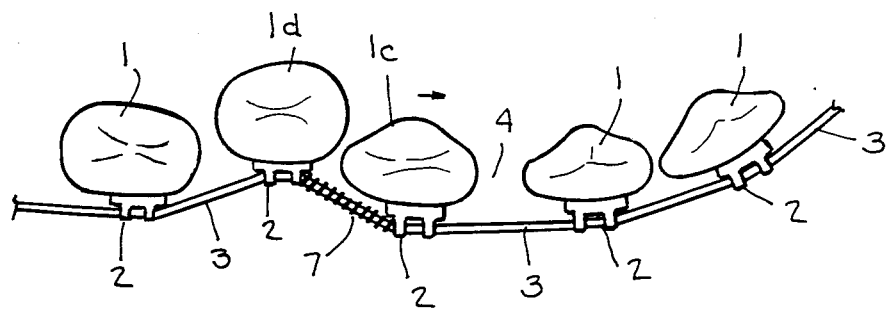
FIG. 1B is a top planar view of another conventional system for orthodontic treatment illustrating the use of a compression coil spring.

The initial tension spring 24 in FIG. 8C may be employed, for example, in place of the conventional spring 6 in FIG. 1A. The end hooks 24a of spring 24 are connected to the stop fittings 5 to move the teeth 1a and 1b into the space 4 and as close to one another as desired. The initial tension in the spring 24 will impart sufficient force with even minimal spring deflection to continue to move the teeth. As a result, and in contrast to the conventional spring 6, only one spring 24 need be employed throughout the entire orthodontic procedure to move the teeth 1a and 1b.

The orthodontic coil springs of the invention, and in particular, the initial tension spring 24, are particularly suited for use in restricted portions of a patient's mouth. By employing the methods as described above, the size of the coil spring of the invention can be minimized, yet the spring force imparted can be maximized by appropriate heat treatment and, or imparting initial tension as described in relation to FIGS. 8A to 8C.

As can be seen, the coil spring of the invention is made to impart a desired spring force by appropriately selecting the heating time within a fixed temperature range necessary to impart superelasticity. Accordingly, the ideal spring force necessary to move a tooth under a particular orthodontic application can be set by simply selecting the appropriate heating time within the temperature range necessary to impart superelasticity.

In the foregoing specification, the invention has been described with reference to particular exemplary embodiments thereof. However, it will be evident that various modifications and changes may be made thereto without departing from the scope of the appended claims. The specification and drawings are, accordingly, to be regarded in an illustrative rather than in a restrictive sense.

What is claimed is:

1. A method of making an orthodontic coil spring for use in imparting forces to move a patient's teeth, said method comprising the following steps:
    winding a shape-memory alloy wire into a coil, and heating said coil for a fixed period of time within a fixed temperature range into a superelastic state for developing a predetermined spring force within a superelastic zone of deflection of said coil.

2. The method of making an orthodontic coil spring according to claim 1, wherein
    the time of heating said coil within said temperature range is decreased in order to increase the spring force of said coil throughout the superelastic zone of deflection of said coil.

3. The method of making an orthodontic coil spring according to claim 1, wherein
    the time of heating said coil within said temperature range is increased in order to decrease the spring force of said coil throughout the superelastic zone of deflection of said coil.

4. The method of making an orthodontic coil spring according to claim 1, wherein
    said shape-memory alloy wire is wound into a coil having a close contact shape for making a tension coil spring.

5. The method of making an orthodontic coil spring according to claim 1, wherein said shape-memory alloy wire is wound into a coil having spaced pitch intervals for making a compression coil spring.

6. A method of making an orthodontic tension coil spring for use in imparting forces to move a patient's teeth, said method comprising the following steps:
   winding a shape-memory alloy wire into a coil having spaced pitch intervals,
   heating said coil for a fixed period of time within a fixed temperature range into a superelastic state for developing a predetermined spring force within a superelastic zone of deflection of said coil, and
   rewinding said coil in the opposite direction of said first winding, and into a coil having a close contact shape so that said coil is formed with initial tension for imparting spring force upon even slight deflection of said coil spring.

7. An orthodontic coil spring for use in imparting forces to move a patient's teeth, said spring comprising:
   a shape-memory alloy wire, said wire being wound into a coil and heat treated into a superelastic state, said coil spring imparting a predetermined spring force within a superelastic zone of deflection of said coil spring.

8. An orthodontic coil spring as described in claim 7, wherein
   said shape-memory alloy wire is made of a nickel-titanium alloy.

9. An orthodontic coil spring as described in claim 7, wherein
   said coil spring imparts a substantially constant spring force throughout a superelastic zone of deflection of said coil spring.

10. An orthodontic tension coil spring for use in imparting forces to move a patient's teeth, said spring comprising:
    a shape-memory alloy wire, said wire being heat treated into a superelastic state and wound into a coil having a close contact shape, said coil having initial tension for imparting a predetermined spring force upon even slight deflection of said coil spring.

11. An orthodontic tension coil spring as described in claim 10, wherein
    said coil spring imparts a substantially constant spring force throughout a superelastic zone of deflection of said coil spring.

* * * * *

UNITED STATES PATENT AND TRADEMARK OFFICE
CERTIFICATE OF CORRECTION

PATENT NO. : 4,849,032

DATED : July 18, 1989

INVENTOR(S) : Kozo Kawaguchi

It is certified that error appears in the above-identified patent and that said Letters Patent is hereby corrected as shown below:

In column 4, line 49, "0.090" should read -- 0.009 --.

In column 4, line 64, "0.090" should read -- 0.009 --.

In column 5, line 16, "spring throughout" should read -- spring force throughout --.

In column 5, line 25, "ooil" should read -- coil --.

In column 5, line 27, "the 3 compression" should read -- the compression --.

Signed and Sealed this

Twenty-seventh Day of November, 1990

Attest:

HARRY F. MANBECK, JR.

*Attesting Officer*         *Commissioner of Patents and Trademarks*

REEXAMINATION CERTIFICATE (1718th)

United States Patent [19]

Kawaguchi

[11] B1 4,849,032
[45] Certificate Issued Jun. 16, 1992

[54] ORTHODONTIC COIL SPRING AND METHOD OF MAKING THE SAME

[75] Inventor: Kozo Kawaguchi, Futaba, Japan

[73] Assignee: Gac International, Inc.

Reexamination Request:
No. 90/001,957, Mar. 14, 1990

Reexamination Certificate for:
Patent No.: 4,849,032
Issued: Jul. 18, 1989
Appl. No.: 169,384
Filed: Mar. 17, 1988

Certificate of Correction issued Nov. 27, 1990.

[51] Int. Cl.$^5$ .............................. C22F 1/10
[52] U.S. Cl. .................. 148/11.5 R; 148/11.5 N; 148/402; 420/902
[58] Field of Search .............. 148/11.5 R, 11.5 N, 148/402; 420/902

[56] References Cited

U.S. PATENT DOCUMENTS 4,037,324 7/1977 Andreasen et al. ................ 433/20
4,490,112 12/1984 Tanaka et al. ..................... 433/20

FOREIGN PATENT DOCUMENTS 57-171653 10/1982 Japan.

OTHER PUBLICATIONS

"The Super-Elastic Property of the Japanese NiTi Wire for Use in Orthodontics", Am. J. Orthod. Dentofacial Orthopedics, Miura, et al., 909 (1): 1-10 (Jul. 1986).
Abstract of "Studies on the Superelastic Japanese NiTi Alloy Coil Springs", 34th Annual Meeting of the JADR (Dec. 4 and 5, 1986).
20 Kirk-Othmer, Encyclopedia of Chemical Technology, 725-736 (3d ed. 1982) New York.
Abstract of "Studies On Mechanical Properties of New Superelastic NiTi Wire", 41st Annual Session of JOS (Sep. 17-19, 1982).
"Characteristics of Deformation and Transformation Pseudoelasticity In NiTi Alloys," Miyazaki, et al., Journal De Physique, vol. C4, No. 12 pp. C4-255-260 (Dec. 1982).

*Primary Examiner*—Richard O. Dean

[57] ABSTRACT

An orthodontic coil spring is made of a shape-memory alloy wire which is wound into a coil and heat treated into a superelastic state. The coil spring imparts a predetermined spring force within a superelastic zone of deflection.

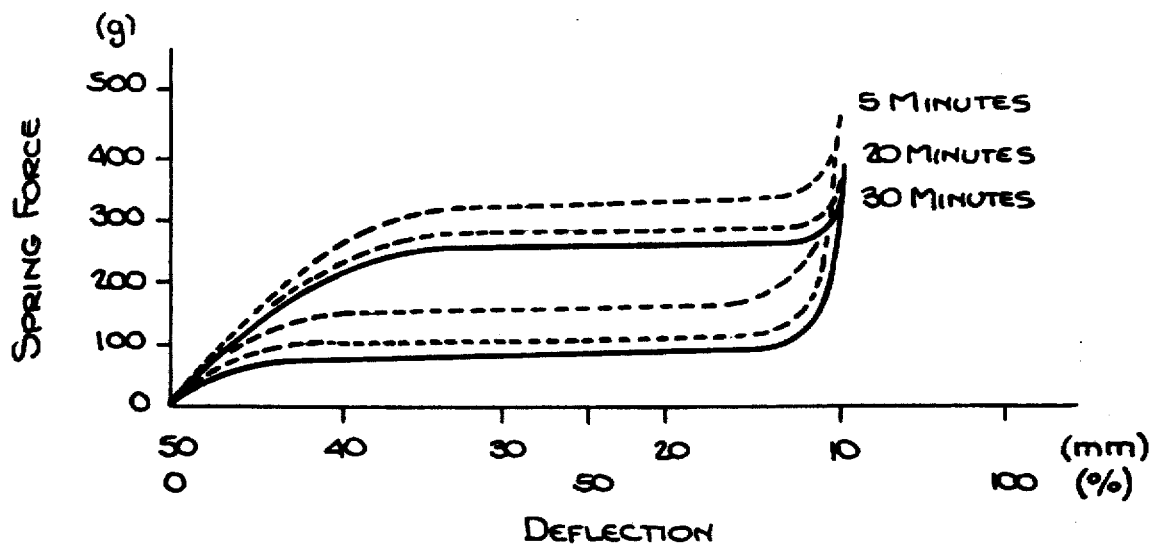

REEXAMINATION CERTIFICATE ISSUED UNDER 35 U.S.C. 307

THE PATENT IS HEREBY AMENED AS INDICATED BELOW.

Matter enclosed in heavy brackets [ ] appeared in the patent, but has been deleted and is no longer a part of the patent; matter printed in italics indicates additions made to the patent.

ONLY THOSE PARAGRAPHS OF THE SPECIFICATION AFFECTED BY AMENDMENT ARE PRINTED HEREIN.

Column 4, lines 27–43:

As shown in FIG. 2, the deflection-spring force curve for a tension coil spring embodying the invention is shown X1, as compared to that for a conventional tension coil spring X2. Similarly, in FIG. 3, the deflection-spring force curve for a compression coil spring Y1 is compared to that for a conventional coil spring Y2. As can be seen in both FIGS. 2 and 3, the springs of the invention impart a substantially constant spring force throughout a relatively wide range of deflection, *approximately 20 mm to 50 mm* known as the superelastic zone of deflection, whereas the spring force of each of the conventional springs increases sharply with increasing deflection. As a result, the coil springs of the invention can be employed to impart a predetermined and substantially constant spring force throughout the entire movement of a tooth, unlike conventional springs which have to be frequently changed or adjusted with incremental tooth movement.

Column 5, lines 3–21:

The coil springs embodying the invention are similar to conventional coil springs in that for a fixed coil spring diameter, the spring force decreases with increasing coil diameter. Likewise, for a fixed coil spring length, the spring force increases with increasing wire diameter. However, unlike conventional coil springs, the spring force of the coil springs of the invention can also be determined depending upon the tooth to be moved, or the particular orthodontic application, by varying the heat treatment time for obtaining superelasticity. Moreover, as described above in relation to FIGS. 2 and 3, and as can be seen in FIGS. 6 and 7, the coil springs embodying the invention each impart a substantially constant spring *force* throughout a superelastic zone of deflection, *approximately 20 mm to 50 mm in FIG. 6 and 12 mm to 40 mm in FIG. 7*. Accordingly, a coil spring embodying the invention can be employed to impart a predetermined and substantially constant spring force throughout the entire movement of a tooth, as described above in relation to FIGS. 2 and 3.

AS A RESULT OF REEXAMINATION, IT HAS BEEN DETERMINED THAT:

The patentability of claim 6 is confirmed.

Claims 1, 7 and 10 are determined to be patentable as amended.

Claims 2–5, 8, 9 and 11 dependent on an amended claim, are determined to be patentable.

New claims 12 and 13 are added and determined to be patentable.

1. A method of making an orthodontic coil spring for use in imparting forces to move a patient's teeth, said method comprising the following steps:
   winding a shape-memory alloy wire into a coil, and heating said coil *at approximately 500° C.* for a [fixed period of] time [within a fixed temperature range] *of approximately 5 to 35 minutes* into a superelastic state for developing a predetermined spring force within *the range of 50 to 300 grams in* a superelastic zone of deflection of said coil *to impart a substantially constant spring force throughout the entire movement of a tooth, said superelastic zone of deflection of said coil spring being within the range of approximately 5 to 30 millimeters and said coil spring substantially returning to its initial length after deflection within the range of said movement of the tooth.*

7. An orthodontic coil spring for use in imparting forces to move a patient's teeth, said spring comprising a shape-memory alloy wire, said wire being wound into a coil and heat treated *at approximately 500° C.* into a superelastic state, *for a time within the range of approximately 5 to 35 minutes,* said coil spring imparting a predetermined spring force within *the range of 50 to 300 grams in* a superelastic zone of deflection of said coil spring *to impart a substantially constant spring force throughout the entire movement of a tooth, said superelastic zone of deflection of said coil spring being within the range of approximately 5 to 30 millimeters and said coil spring substantially returning to its initial length after deflection within the range of said movement of the tooth.*

10. An orthodontic tension coil spring for use in imparting forces to move a patient's teeth, said spring comprising:
   a shape-memory alloy wire, said wire [being] *having been wound into a coil having spaced pitch intervals and* heat treated into a superelastic state and *then* wound into a coil *in the opposite direction* having a close contact shape, said coil *thus* having initial tension for imparting a predetermined spring force upon even slight deflection of said coil spring.

*12. A method of making an orthodontic closed coil spring for use in imparting forces to move teeth, the method comprising the following steps:*
   *winding a shape-memory alloy wire into an open coil;*
   *heating the coil at approximately 500° C. for a time approximately within the range of 5 to 35 minutes for developing a predetermined spring force within the range of 50 to 300 grams within a superelastic zone of deflection starting at a slight deflection of said coil spring; and*
   *rewinding the open coil in the opposite direction of the first winding into a closed coil, the closed coil spring thus being formed with initial tension for imparting a spring force within the range of 50 to 300 grams in response to a slight amount of deflection of said coil spring.*

*13. An orthodontic closed coil spring for use in imparting forces to move teeth, comprising:*
   *a shape-memory alloy wire wound into a closed coil, the wire having initially been wound into an open coil and heated at approximately 500° C. for a time approxi-* mately within the range of 5 to 35 minutes, the open coil then having been wound in the opposite direction of the first winding into a closed coil, the closed coil spring thus being adapted to impart a substantially predetermined spring force within the range of 50 to 300 grams in a superelastic zone of deflection starting at a slight amount of deflection of said coil spring.

* * * * *